United States Patent
Delogé et al.

(10) Patent No.: US 6,783,535 B2
(45) Date of Patent: Aug. 31, 2004

(54) TARGETING APPARATUS FOR USE IN PERFORMING ENDOFEMORAL OSTEOTOMY SURGERY

(75) Inventors: Nicolas Delogé, Douvres (FR); Jean-Pierre Brée, Fontaine Etoupefour (FR); Arnaud Aux Epaules, Saint-aubin-sur-mer (FR); Philippe Lavieille, Caen (FR); Christophe Cueille, Missy (FR)

(73) Assignee: Benoist Girard SAS (FR)

( * ) Notice: Subject to any disclaimer, the term of this patent is extended or adjusted under 35 U.S.C. 154(b) by 116 days.

(21) Appl. No.: 10/008,336

(22) Filed: Nov. 8, 2001

(65) Prior Publication Data

US 2003/0018341 A1 Jan. 23, 2003

(30) Foreign Application Priority Data

| Nov. 13, 2000 | (GB) | 0027698 |
| Nov. 13, 2000 | (GB) | 0027700 |
| Mar. 8, 2001 | (GB) | 0105779 |
| Oct. 9, 2001 | (GB) | 0124230 |

(51) Int. Cl.⁷ ............................ A61B 17/56
(52) U.S. Cl. ...................................... 606/98
(58) Field of Search ................... 606/86, 97, 98, 606/80, 64

(56) References Cited

U.S. PATENT DOCUMENTS

| 2,362,957 A | | 9/1941 | Hackett |
| 3,945,377 A | | 3/1976 | Kronner |
| 4,037,592 A | | 7/1977 | Kronner |
| 4,187,840 A | | 2/1980 | Watanabe |
| 4,541,424 A | | 9/1985 | Grosse et al. |
| 4,667,664 A | | 5/1987 | Taylor et al. |
| 4,865,025 A | | 9/1989 | Buzzi et al. |
| 4,881,535 A | * | 11/1989 | Sohngen ............... 606/98 |
| 4,883,048 A | | 11/1989 | Purnell et al. |
| 4,911,153 A | * | 3/1990 | Border ................ 606/98 |
| 5,078,719 A | | 1/1992 | Schreiber |
| 5,176,681 A | | 1/1993 | Lawes et al. |
| 5,207,682 A | | 5/1993 | Cripe |
| 5,306,278 A | | 4/1994 | Dahl et al. |
| 5,334,192 A | | 8/1994 | Behrens |
| 5,374,271 A | | 12/1994 | Hwang |
| 5,403,322 A | | 4/1995 | Herzenberg et al. |
| 5,620,449 A | | 4/1997 | Faccioli et al. |
| 5,649,930 A | * | 7/1997 | Kertzner ............... 606/96 |
| 5,665,086 A | | 9/1997 | Itoman et al. |
| 6,027,506 A | | 2/2000 | Faccioli et al. |
| 6,102,953 A | | 8/2000 | Huebner |
| 6,168,628 B1 | | 1/2001 | Huebner |
| 6,494,913 B1 | | 12/2002 | Huebner |
| 2002/0095159 A1 | * | 7/2002 | Deloge et al. ......... 606/98 |
| 2002/0133172 A1 | * | 9/2002 | Lambrecht et al. ..... 606/130 |

FOREIGN PATENT DOCUMENTS

| DE | 296 12 306 | 2/1997 |
| EP | 0 514 662 A | 4/1992 |
| FR | 2 647 006 | 5/1989 |
| FR | 2 686 788 | 2/1992 |
| FR | 2 692 472 | 12/1993 |
| JP | 09075366 | 3/1997 |
| WO | WO 92/01422 | 2/1992 |

* cited by examiner

Primary Examiner—Eduardo C. Robert
(74) Attorney, Agent, or Firm—Lerner, David, Littenberg, Krumholz & Mentlik, LLP

(57) ABSTRACT

A targeting apparatus for use in performing endofemoral osteotomy surgery has a support element provided with a drill guide. The apparatus has a connector for securing a support element to the proximal end of a prosthesis to be implanted. The apparatus includes a proximal location element which is shaped to extend around the great trochanter and muscle of the femur in which the implant is to be located. An adjustor is provided for adjusting the angular position of the drill guide in relation to the femur about a proximal-distal axis.

23 Claims, 11 Drawing Sheets

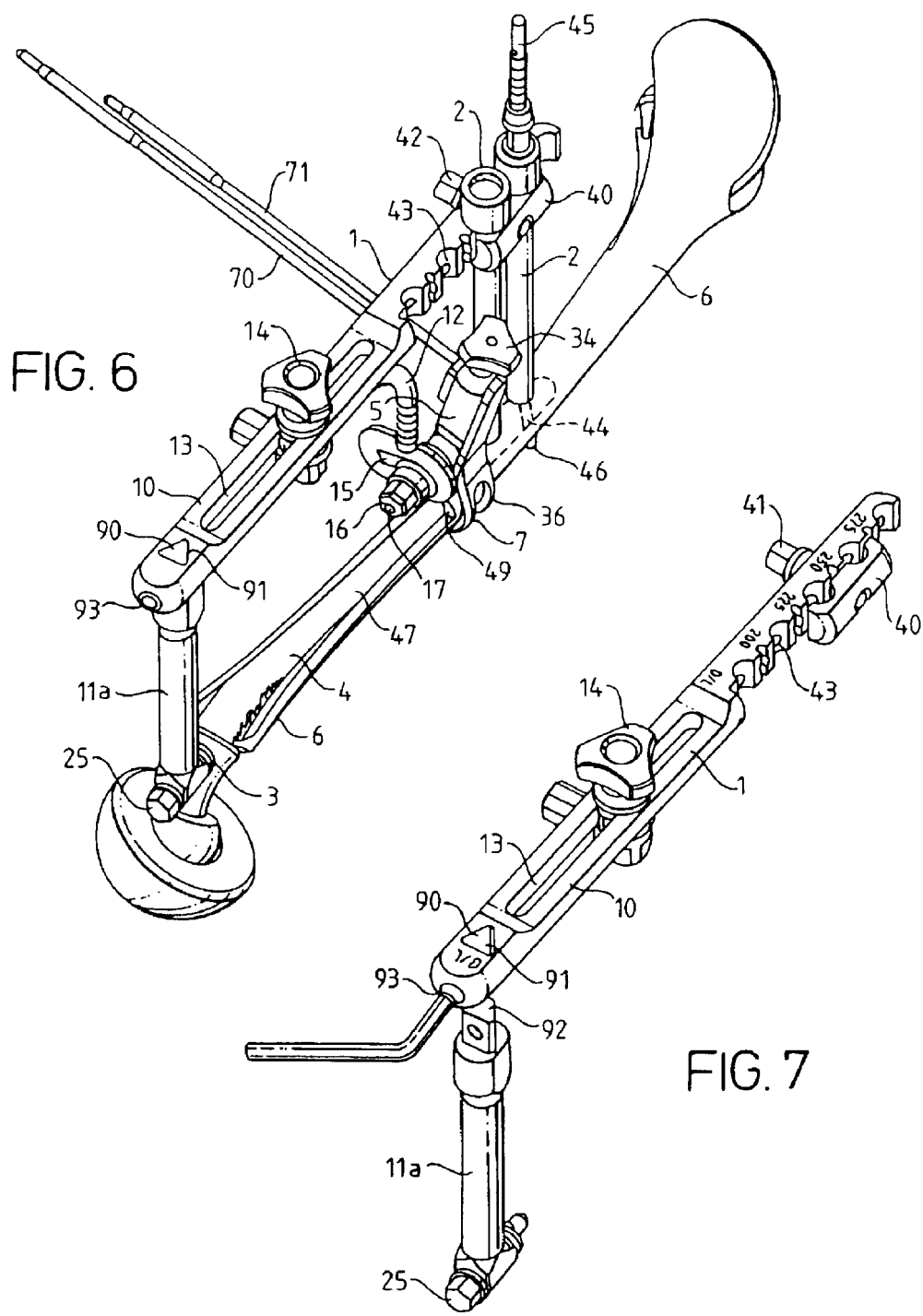

TARGETING APPARATUS FOR USE IN PERFORMING ENDOFEMORAL OSTEOTOMY SURGERY

BACKGROUND OF THE INVENTION

This invention relates to a targeting apparatus for use in performing endofemoral osteotomy surgery. The apparatus is also suitable for conversion so that it can be used in transfemoral osteotomy surgery. In this particular surgical technique the femur is exposed along a proximal-distal line, the soft tissue (skin, muscle) being folded back on each side to expose the bone. The proximal end of the femur is now opened as a "window" and a femoral prosthesis is inserted into the bone canal.

As mentioned above, the present invention is capable of being used with both surgical approaches if converted.

There are difficulties in both techniques in assessing the particular angular position of the prosthesis in the femoral canal and the exact location of the resectioning of the femur must be accurately judged. A further difficulty arises with regard to the placement of one or more retaining bolts towards the distal end of the stem of the prosthesis. These bolts or pins pass through the bone, the stem of prosthesis and out through the other side of the bone thus anchoring the prosthesis in position. It is difficult for surgeons to judge the exact position to drill the holes in the bone to coincide with the holes in the implant and it is also necessary to select the correct angular position of the prosthesis and therefore the holes. It is also difficult for the surgeon to judge the exact distance down the femur for the holes to achieve the correct leg length of the correction.

The present invention is intended to overcome some of the difficulties referred to above and to provide apparatus which will achieve a more accurate surgical technique.

SUMMARY OF THE INVENTION

According to the present invention targeting apparatus for use in performing endofemoral osteotomy surgery comprises a support element provided with a drill guide, a connector for securing the support element to the proximal end of the prosthesis to be implanted and which include a proximal location element which is shaped to extend around the great trochanter and muscles of the femur in which the implant is to be located, and an adjustor for adjusting the angular position of the drill guide in relation to the femur about a proximal-distal axis.

Thus, the apparatus can be used to accurately locate the angular position of the drill guide and the prosthesis (anteversion setting) and which can be used to drill the holes to take the retaining bolt or bolts in the bone.

Preferably the proximal location element is in the form of a curved arm connected to the support element and this arm can be substantially S-shaped.

The proximal location element can be arranged to be detachable from the support element, for example, by use of a plug and socket connection, and this can be of a triangular cross-section.

Two detachable alternative proximal location elements can be provided, one for use with a right femur and the other for use with a left femur.

The targeting apparatus according to the invention can also be used for performing transfemoral osteotomy surgery by the provision of suitable conversion features. Thus, the apparatus can include conversion means for converting it for use in performing transfemoral osteotomy surgery.

The conversion means can include a connector for securing the support element to a resectioned femur to allow this form of surgery to be carried out.

Alternative devices are also provided for securing the support element to the prosthesis to be implanted and which is adapted to replace the shaped proximal location element.

This alternative device may comprise a substantially straight proximal arm adapted for connection to the support element.

When converted in this way the apparatus can embody the features set forth in British Patent Application Nos. 00 27698.0 filed Nov. 13, 2000, 00 27700.4 filed Nov. 13, 2000 and 01 05779.3 filed Mar. 8, 2001.

The invention also includes a kit of parts to provide targeting apparatus for use in performing endofemoral and/or transfemoral osteotomy surgery comprising a support element provided with a drill guide, a connector for securing the support element to a prosthesis to be implanted when performing endofemoral surgery and which includes a proximal location element which is shaped to extend around the great trochanter and muscles of the femur, alternative connectors for securing the support element to a prosthesis to be implanted when performing transfemoral surgery, an adjuster for adjusting the angular position of the drill guide in relation to the resectioned femur about a proximal/distal axis, and a connector for securing the support element to a femur.

The kit of parts can also include a drill guide element which has a line of drill guide openings each of which is adapted to guide a drill and a connector for rigidly securing the drill guide element to the connector for securing the support element to a femur.

Also included in the kit of parts can be a drill guide for drilling openings through the bone and soft tissue when it has been folded back into position at the proximal end of the femur when conducting the transfemoral surgery.

BRIEF DESCRIPTION OF THE DRAWINGS

The invention can be performed in various ways and some embodiments will now be described by way of example and with reference to the accompanying drawings in which:

FIG. 6 is an isometric view from above of the apparatus shown in FIG. 1 when converted for use when performing transfemoral osteotomy surgery and in position on the femur;

FIG. 7 is an isometric view from above showing part of the apparatus shown in FIG. 6 with the proximal location element detached;

DETAILED DESCRIPTION OF THE PREFERRED EMBODIMENT

In endofemoral osteotomy surgery the proximal end of the femur is resectioned by removing its proximal end. The stem of the prosthetic implant is inserted into the proximal end of the bone canal and accurately located by the surgeon. The exact position of the femur must be accurately judged and the distal end of the stem of the implant usually carries one or more openings through which one or more retaining bolts are passed. Thus these bolts pass through the bone and the implant to anchor the stem of the prosthesis.

It is difficult for surgeons to judge the exact position to drill the holes so as to coincide with the holes in the implant and to select the correct angular position. The position of the holes also controls the corrected leg length.

Figure 1:
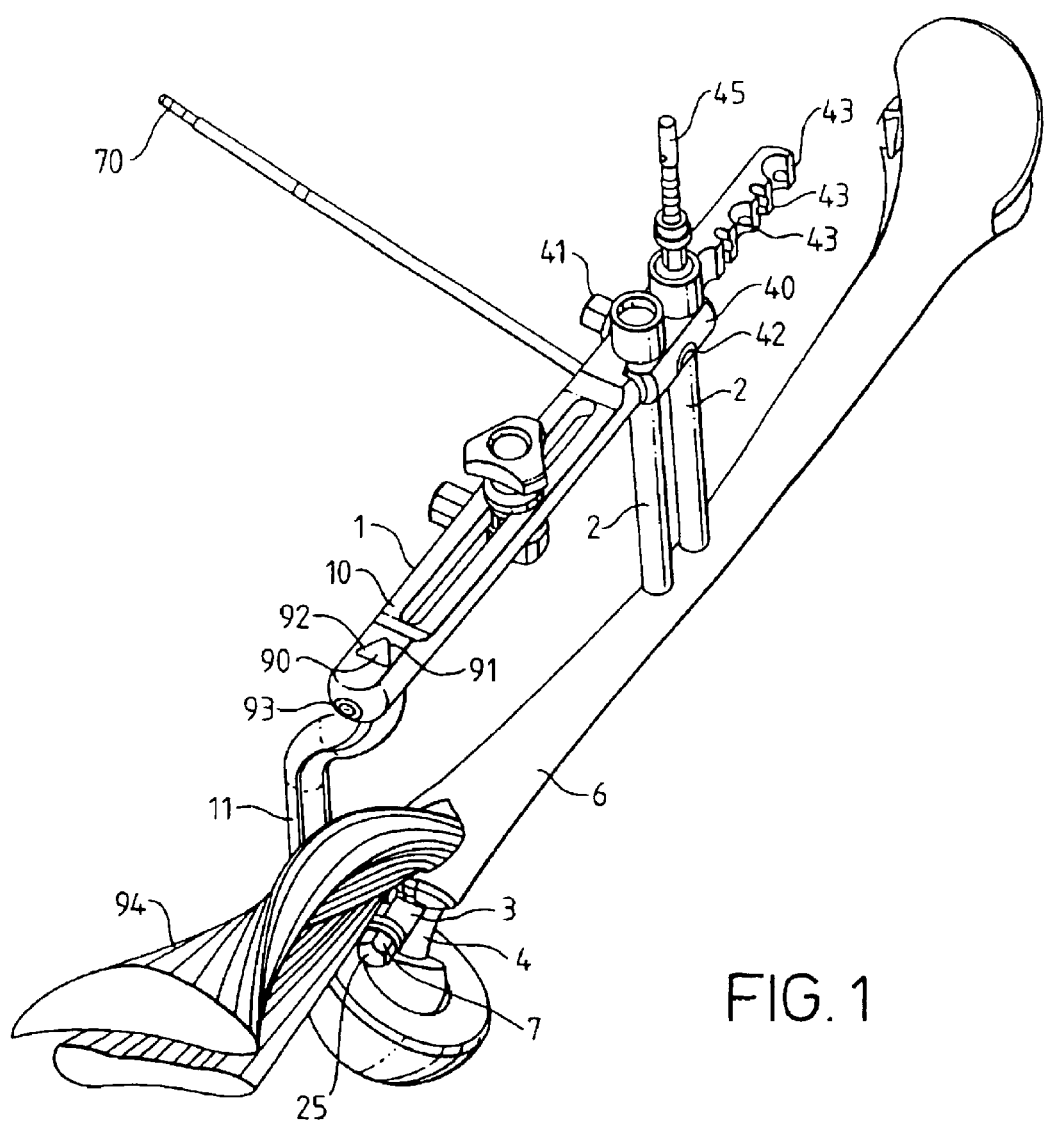
FIG. 1 is an isometric view from above showing the layout of the targeting device according to the present invention when set up for use in performing endofemoral osteotomy surgery.

FIG. 1 shows a targeting apparatus for use in performing endofemoral osteotomy surgery and this comprises a support element 1 provided with two drill guides 2 and a connector 3 for securing the support element 1 to a prosthesis 4 which is to be implanted in a resectioned femur which is indicated by reference numeral 6. An adjuster 7 is included for adjusting the angular position of the drill guides 2 in relation to the resectioned femur 6 about a proximal-distal axis.

The support element 1 is in the form of an L-shaped frame which has a first arm 10 and a second proximal location element provided by a curved arm 11. As will be seen from FIGS. 1, 2 and 3 curved arm 11 is substantially S-shaped. Thus first arm 10 carries drill guides 2 and the proximal location element provided by the S-shaped arm 11 carries connector 3 for connecting the support element 1 to the proximal end of the femoral prosthesis.

Figure 8:
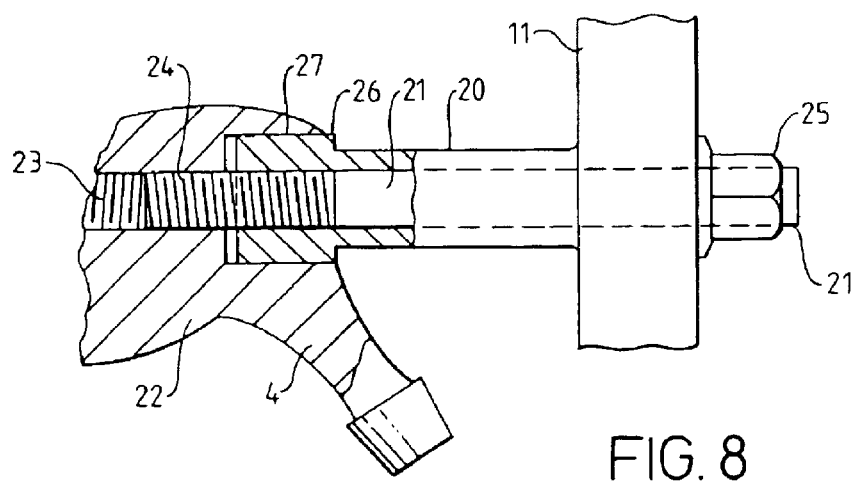
FIG. 8 is a part cross-sectional view of the connector for securing the support element of the apparatus shown in the preceding figures to a prosthesis to be implanted.

Connector 3 for connecting support element 1 to the femoral prosthesis through the proximal location element provided by the S-shaped arm 11 is shown in more detail in FIG. 8 and comprises a sleeve 20 secured to S-shaped arm 11 and in which is located a securing stud 21.

The proximal end 22 of the prosthesis 4 is provided with a screw threaded bore 23 in which a screw threaded portion 24 of the stud 21 can be located. The other end of the stud is held by a nut 25.

The distal end of sleeve 20 is provided with a pair of opposed projecting keys 26 which engage in keyways 27 in the form of slots provided in an enlarged end portion of bore 23.

Thus, it will be seen that prosthesis 4 can be held in position on S-shaped arm 11 and be restrained against relative rotation by the keys 26 and the keyways 27.

Drill guides 2 are carried on arm 10 by a clamping plate 40 which is held in place by a screw threaded shaft 41 which engages a screw thread 42 in the clamping plate. The screw threaded shaft 41 passes through a series of openings 43 in arm 10. As will be seen from the drawings, once the guides have been fixed in position there is a predetermined distance from the guides to connector 3 for connecting support element 1 to the femoral prosthesis 4. This distance can however be adjusted by using alternative openings 43. Drill guides 2 are set for a position with respect to the given prosthesis so that they are fixed and aligned with the holes (not shown in FIGS. 1 and 2) in prosthesis 4.

Figure 2:
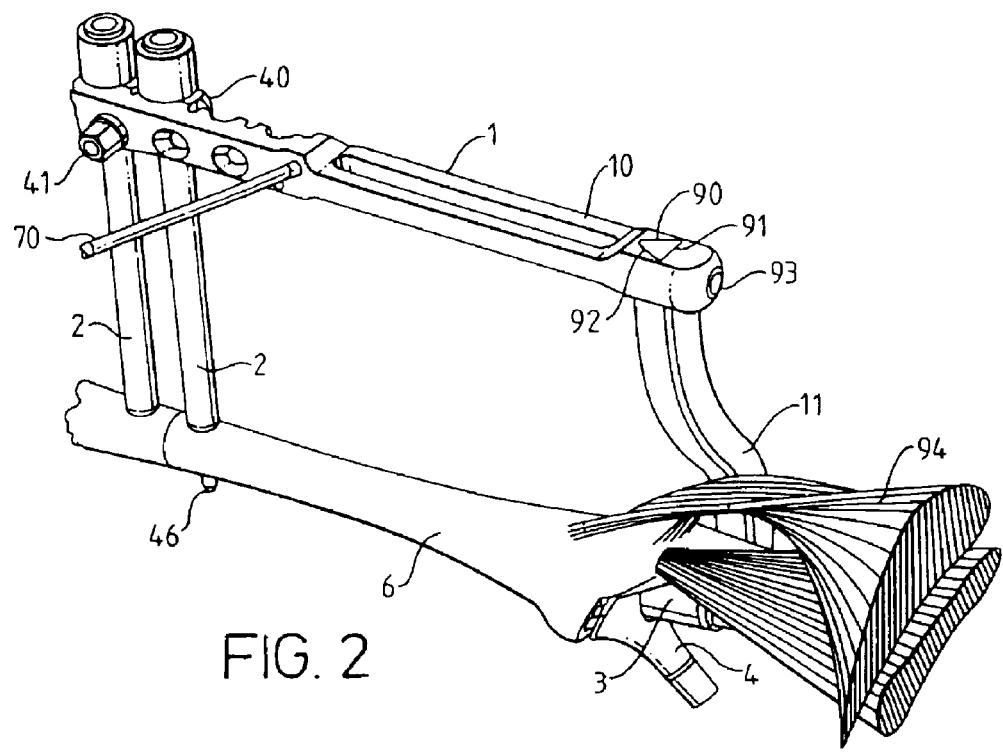
FIG. 2 is an isometric view from a first side of part of the apparatus shown in FIG. 1.

A typical drill bit 45 is shown in place in one of the drill guides 2 and its lower operative end 46 (as shown in FIG. 2) indicate how it has been drilled through the femur 6 passing through the existing holes in the stem of the prosthesis and through the other side of the femur 6.

The proximal location element in the form of the S-shaped arm 11 is detachable from the support element 1 and is secured by a plug and socket connection indicated by reference numeral 90. A triangular socket 91 is provided in arm 10 into which a triangular shaped plug 92 is inserted. This construction is more clearly shown in FIG. 7.

The plug 92 is retained in position by a locking screw 93 in the end of the arm.

The proximal location element in the form of the S-shaped arm 11 is shaped to extend around the great trochanter and muscles (indicated by reference numeral 94 in FIGS. 1 to 3) of the femur hip joint in which the implant is to be located. This enables a frame of the type described above to be employed.

Two S-shaped arms 11 are provided, one for use with a right femur and the other for use with a left femur, the appropriate arm being used.

To carry out the surgery relating to endofemoral osteotomy the surgeon first ensures that appropriate X-rays have been taken so that he can consider the amount of bone which needs to be removed from the femur. Once this has been decided the measurements are carefully taken for further use with the apparatus according to the invention.

The femur is appropriately resectioned and the prosthesis is inserted. It is then connected to the targeting device by means of connector 3 for connecting it to the support element 1. With the support element 1 now suitably connected it is rotated axially about a proximal-distal axis of the femur until the correct position of the drill guides 2 is achieved. They will have been previously set to an appropriate and predetermined position on the proximal-distal axis. A visual indicator guide arm 70 is attached to the L-shaped frame in the form of a rod and this can also be employed to achieve the correct position. With the targeting device accurately located the surgeon can drill the requires holes in the femur 6 and this can be done without interfering with the muscle 94.

Figure 3:
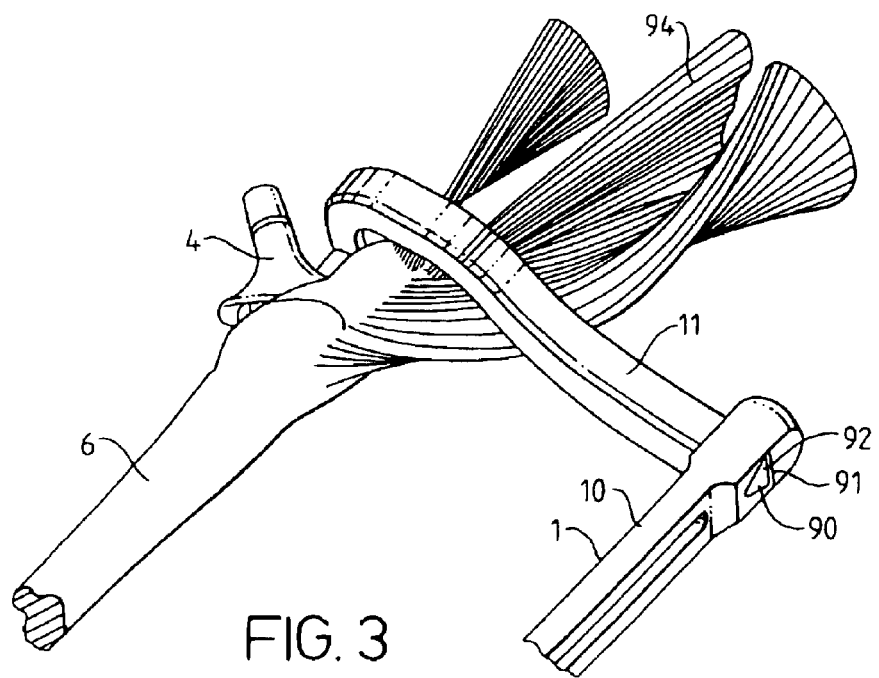
FIG. 3 is an isometric view of part of the apparatus from the side opposite that shown in FIG. 2.

The targeting apparatus shown in FIGS. 1 to 3 can also be employed for performing transfemoral osteotomy surgery by adding additional components.

In this surgical technique the femur is exposed along a proximal-distal line, the soft tissue (skin, muscle) being folded back on each side to expose the bone. The proximal end of the femur is now opened as a "window" and a femoral prosthesis is inserted into the bone canal.

Figure 4:
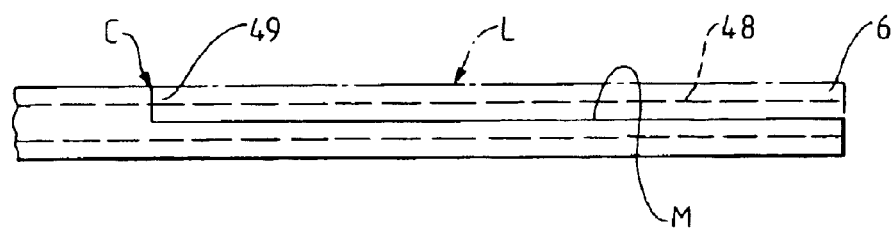
FIG. 4 is a diagrammatic side view of a femur showing how it is cut for performing transfemoral osteotomy surgery.
Figure 5:
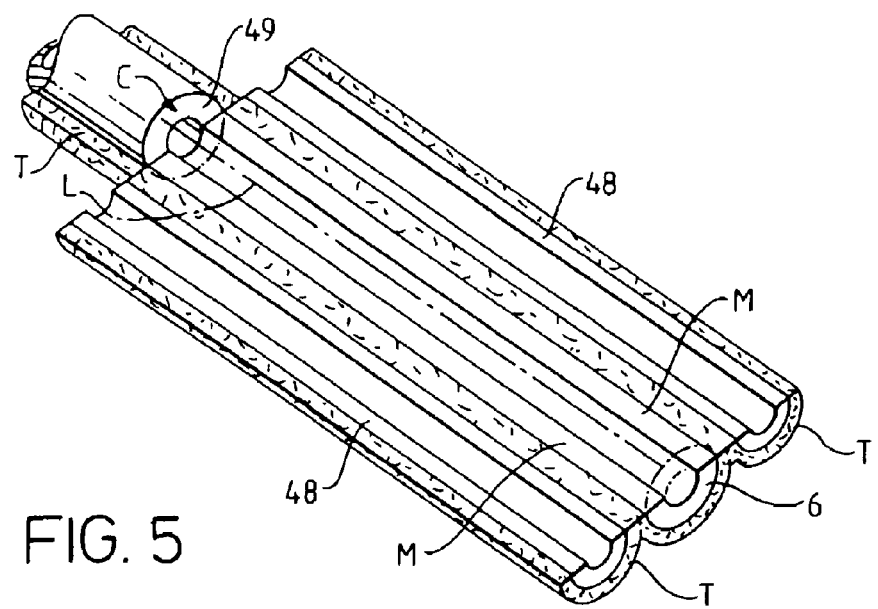
FIG. 5 is a diagrammatic perspective view showing how the "window" is formed in the femur for transfemoral osteotomy surgery.

FIGS. 4 and 5 show, in simplified form, how transfemoral osteotomy surgery is performed. The soft tissue indicated by reference letter T in FIG. 5 is exposed along a proximal/distal line indicated by chain line L in FIG. 5. The soft tissue T is folded back on each side to expose the femur 6 and the bone is resected with three cuts along the same line L two side cuts M and with a transverse cut C. The proximal end of the femur is now opened, as shown in FIG. 5, as a "window." From FIG. 5 it will be seen that an upper quarter 48 is now laid on each side of the remaining part of the bone to expose the bone canal into which the prosthesis is to be inserted.

FIGS. 6 and 7 show how additional or substituted parts are used with the targeting apparatus as shown in FIGS. 1 to 3 so that it can be converted for use in performing transfemoral osteotomy surgery.

In FIGS. 6 and 7 the same reference is used to indicate similar parts to those shown in FIGS. 1 to 2 but the S-shaped arm 11 is substituted by a substantially straight proximal arm 11a which is provided with the same type of plug and socket 50 and connector 3. Additionally femur connector or clamp 5 are provided which are connected to the first arm 10 by an adjustable bracket 12 which can be adjusted in proximal-distal directions only in a slot 13 in the arm 10 and locked in position by a retaining nut 14, and the femur connector 5 can be angularly adjusted in relation to bracket 12 in a slot 15 provided on the bracket and locked in position by a nut 16.

The nut 16 is carried on a screw threaded boss indicated by reference numeral 17 is carried on the femur clamp 5.

Figure 9:
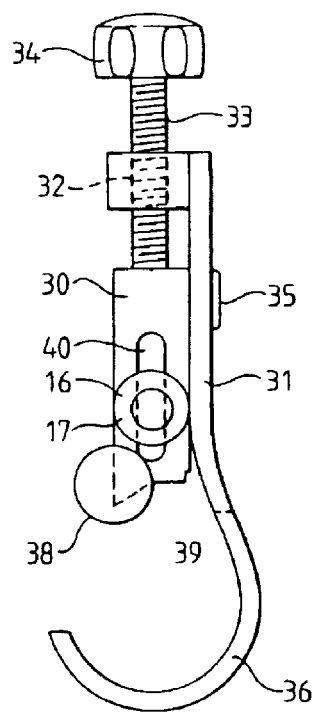
FIG. 9 is a side elevation of a clamp device shown in FIG. 6 for securing the support element to a resectioned femur.
Figure 10:
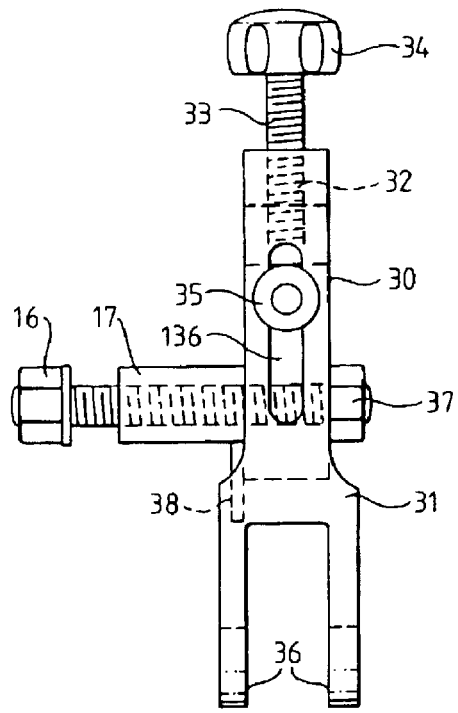
FIG. 10 is a front elevation of the clamp device shown in FIG. 9.

Connector or clamp 5 for securing the support element to a resectioned femur 6 is most clearly shown in FIGS. 9 and 10 and comprises an open-jawed clamp device. This device has a main body portion 30 on which is located a movable clamping jaw 31. The upper part of the clamping jaw 31 has a screw threaded bore 32 which houses a threaded member 33 one end of which carries an operating handle 34 and the other end of which is rotatably housed in the body 30. Thus, rotation of the handle 34 raises and lowers the clamp 31 which is also located by a retaining screw 35 which passes through a slot 136.

The lower end of the open jawed clamp is formed as a pair of curved tines 36 which are adapted to extend around the resectioned femur to which the device is to be clamped.

A guide in the form of a disc 38 mounted on body 30 are provided, the disc projecting below the lower end 39 of the body 30.

The boss 17 is located in a slot 40 in the body 30 and held by a nut 37 but is free to move so that the position of the clamp adjusts itself in relation to the adjustment bracket 12 to alter the radial distance from the femur 6.

In order to clarify the drawings in FIG. 6 the soft tissue T and bone which has been folded back to provide the "window" and expose femur 6 is not shown but the femur will be in the condition shown in FIG. 5.

To carry out the surgery relating to a transfemoral osteotomy the surgeon first ensures that appropriate X-rays have been taken so that he can consider the amount of bone which needs to be removed from the femur. Once having decided this the measurements are carefully taken for further use with the apparatus according to the invention.

The "window" is now opened to reveal the femur and the bone is cut appropriately to provide a proximal end C, indicated by reference numeral 49 in FIG. 5. The clamp 5 is now located in position on the end of the femur by tucking it around the femoral end and ensuring that the guide disc 38 is close up against the severed end 49. The positioning is achieved with a rotative movement. Once in place the handle 34 is operated to close the clamp and retain it in place. The stem (not shown) of the prosthesis 4 is now inserted in the femoral canal and the frame in the form of the arms 10 and 11 is connected to it by means of the connector 3.

The nut 14 is released to allow the bracket 12 to move in slot 13 and so that it can be secured to femur clamp 5 by the boss 17 and nut 16 through the slot 15. The release of nut 16 allows slot 15 to be placed on boss 17 at the appropriate radial distance from the femur prior to subsequent tightening. It will be appreciated that the proximal-distal movement in slot 13 accommodates the leg length adjustment. The ante/retroversion (version angle) adjustment is now carried out by revolving the frame about axis of the prosthesis 4 and the particular angle adjustment is set by tightening nut 16. During this angular movement prosthesis 4 which is securely attached to the support frame revolves with it as do drill guides 2.

The proximal-distal positioning of the drill guides is set according to the pre-operative planning and they are now positioned by releasing nut 42 so that they can be located in contact with the cortex of the femur and the nut suitably tightened.

The drill guides can now be used to produce the necessary holes through the bone to accept the required bolts or pins.

In the arrangement described above two drill guides are shown but only one or any other number can be utilized if required.

The apparatus can be simply removed by releasing the stud 21 in prosthesis 4, releasing the nut 16 and removing the frame. The clamp 5 can be removed separately.

The "window" is now closed according to any known post-operative technique.

Figure 11:
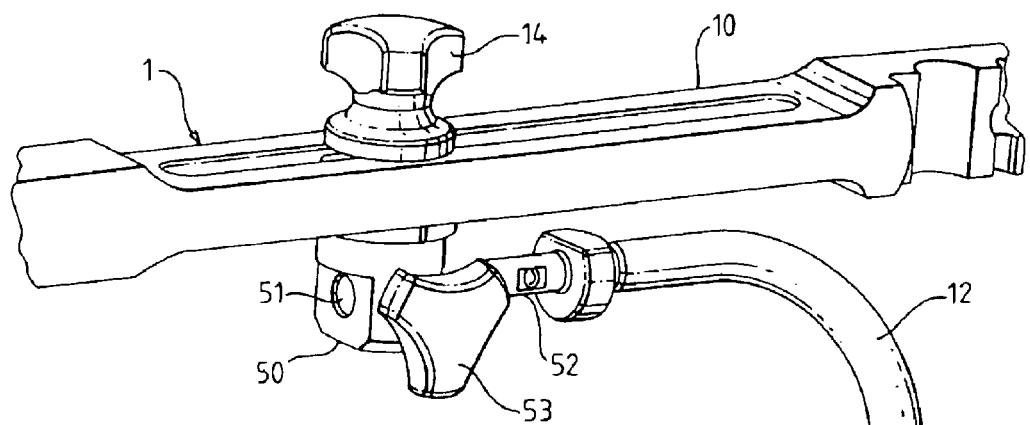
FIG. 11 is an isometric view of part of the support element.

FIG. 11 shows an alternative embodiment in which the same reference numerals are used to indicate similar parts. In this arrangement adjustable bracket 12 can be readily disconnected from first arm 10 of the L-shaped frame. In this construction nut 14 is shown as a hand nut and is carried on a boss 50 which has a bore 51 adapted to receive a spigot 52 provided on the end of the bracket 12. Boss 50 also carries a screw threaded locking nut 53 which can be advanced through a screw threaded bore (not shown) so that it engages against the spigot 52 where it is located in bore 51 to clamp it in position. This construction enables disconnection of the assembly without having to unscrew locking nut 14 thus enabling the leg length to be set without readjustment.

Figure 12:
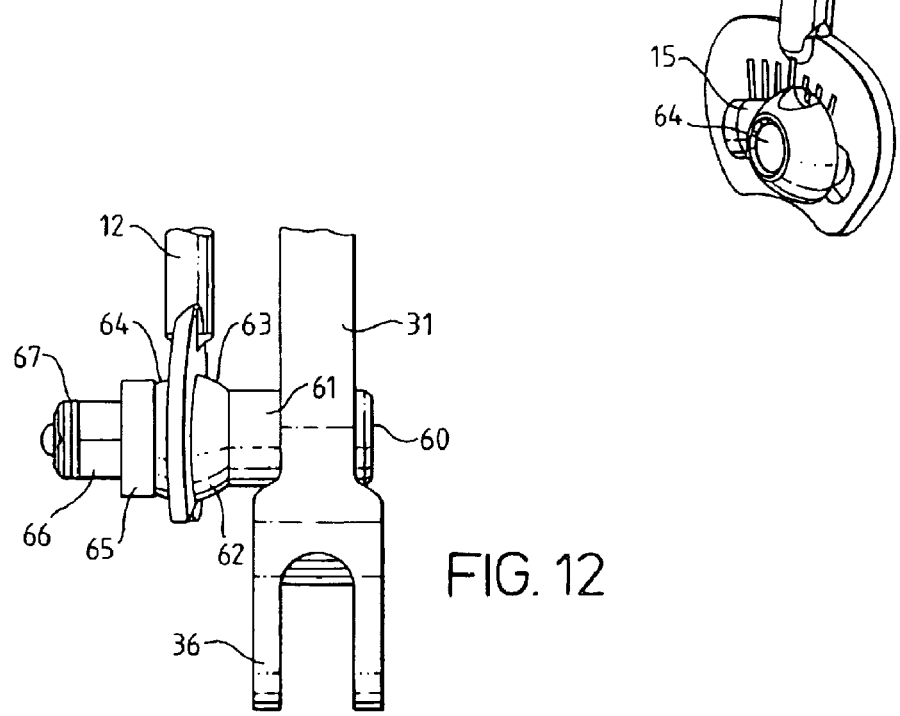
FIG. 12 is a partial side view of an alternative embodiment of the clamp device shown in FIGS. 9 and 10.
Figure 13:
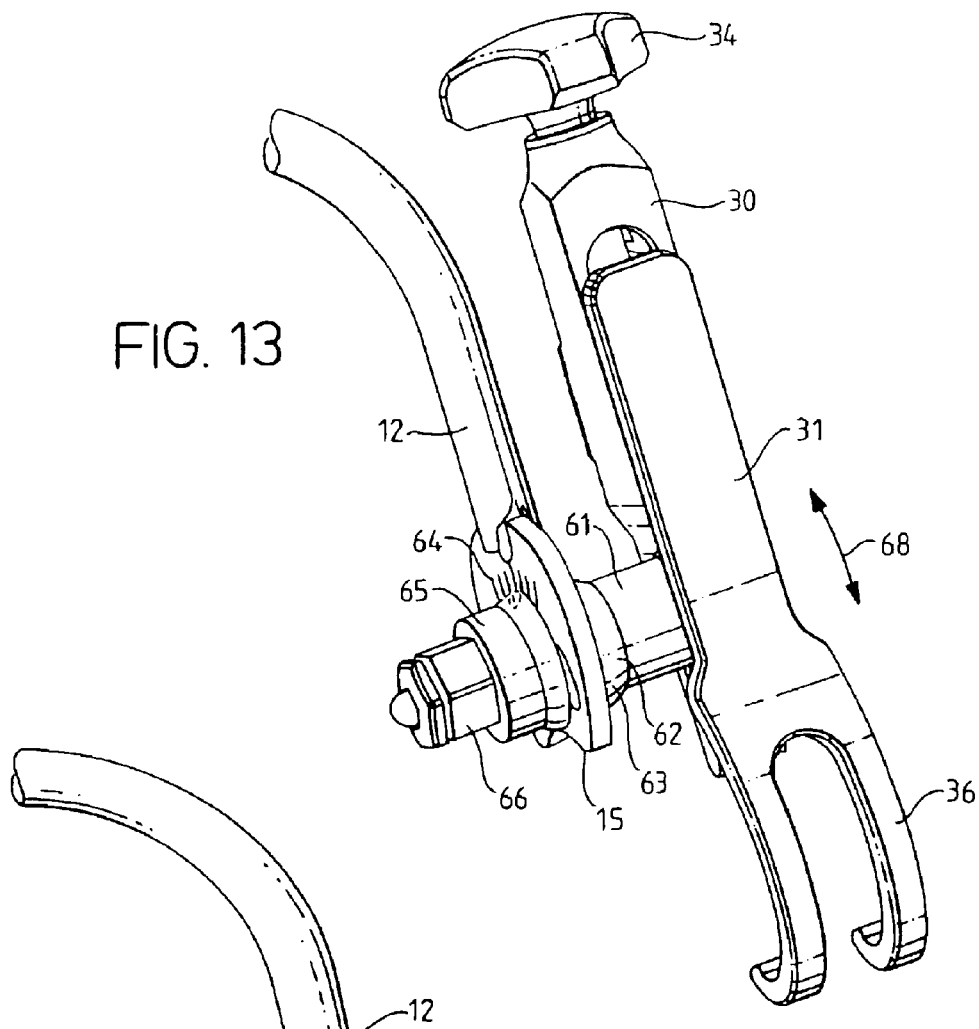
FIG. 13 is an isometric view of the embodiment shown in FIG. 12.
Figure 14:
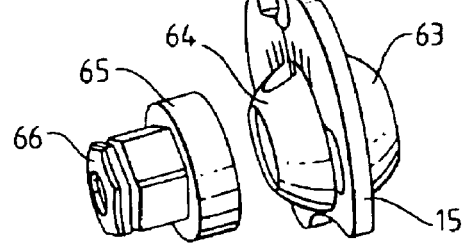
FIG. 14 is an isometric view of the construction shown in FIG. 13 partially dissembled.

FIGS. 12, 13 and 14 show an embodiment construction for the open jawed clamp device and the same reference numerals are used to indicate similar parts to those shown in FIGS. 9 and 10. In this embodiment however, the boss 17 is replaced by a bolt 60 which extends through the slot 40 and carries a spacer 61. One end 62 of the spacer is dished to accommodate a part-spherically shaped washer 62. A second part spherically-shaped washer 64 is also located on the screw 60 and one side of this is housed in a dished portion 65 of the nut 66. The nut 66 has a circumferential groove 67 to accommodate resilient ring (not shown) which can act to retain a socket wrench during assembly. Each of the washers 64 and 63 also has a flat side which are located against the sides of slot 15 on bracket 12 when the whole construction is assembled together with screw 60 passing through the slot 15.

With nut 66 tightened, the assembly is tightly clamped together, but if the nut 66 is slackened the bracket 12 can align itself in three different directions by a movement of the part spherical washers in the spacers 61 and 65. This enables three relative rotations, one of which is the anteversion setting on the other two rotations enable centering of the stem in the femur if the clamp is ill positioned on it.

As the attachment of the clamp to bracket 12 is also adjustable and can be clamped in position movement of the clamp in the direction of the arrows 68 on FIG. 13. This enables the automatic adoption of the femur diameter and once set can be tightly adjusted to provide rigidity of the assembly.

Figure 15:
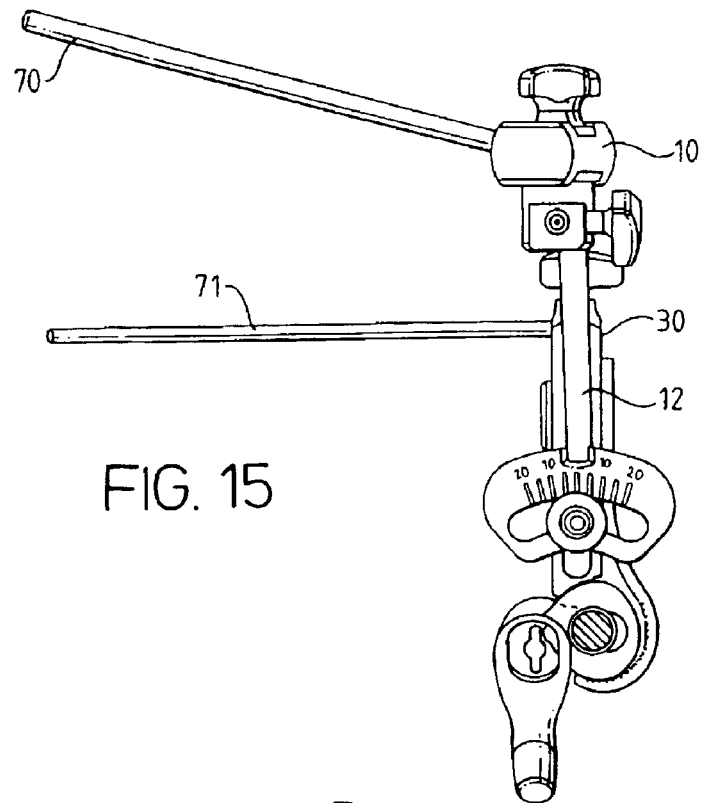
FIG. 15 is an end view of the device shown in FIG. 11 incorporating the alternative constructions shown in FIGS. 12, 13 and 14 and including visual indicator guides with the support element in a first position.

FIG. 15 shows how visual indicator guides can be provided. Thus, a visual indicator guide arm 70 is attached to the L-shaped frame 10 in the form of a rod which extends at 150 to the axis of the first arm 10. A second indicator guide 71 which is also in the form of a rod is attached at an angle normal to the longitudinal axis of the clamp main body portion 30.

Figure 16:
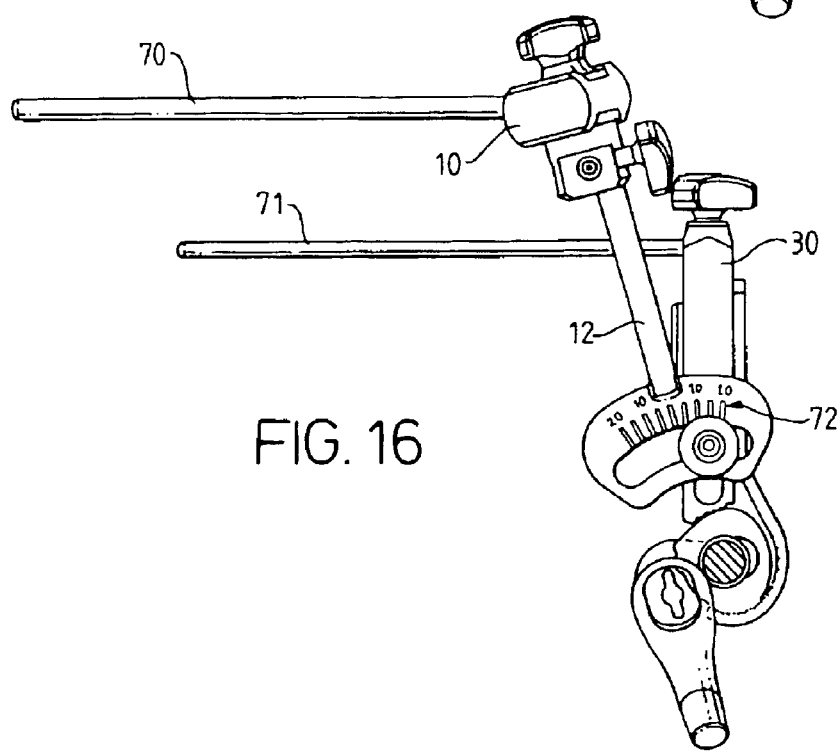
FIG. 16 is a similar view to FIG. 15 with the support element in a second aligned position.

Using the visual indicator guides the apparatus is placed in position with the clamp positioned perpendicular to the 90° knee flexion plane. This is the first position of the anteversion at 0° and this is shown in FIG. 15. In FIG. 16 the L-shaped frame 10 has been rotated until the visual indicator guides 70, 71 are parallel. In this position the frame 10 has been rotated through 15° in relation to the clamp 30. Thus, the neck axis is parallel to the axis of the frame 10 and the rotation of the frame has thus created an angle between the clamp and the frame which is the anteversion angle. The exact angle of anteversion can be read from a scale indicated by reference numeral 72 provided on the bracket 12.

The standard value of anteversion is 15° and this can be used as a datum when setting up the apparatus.

Figure 17:
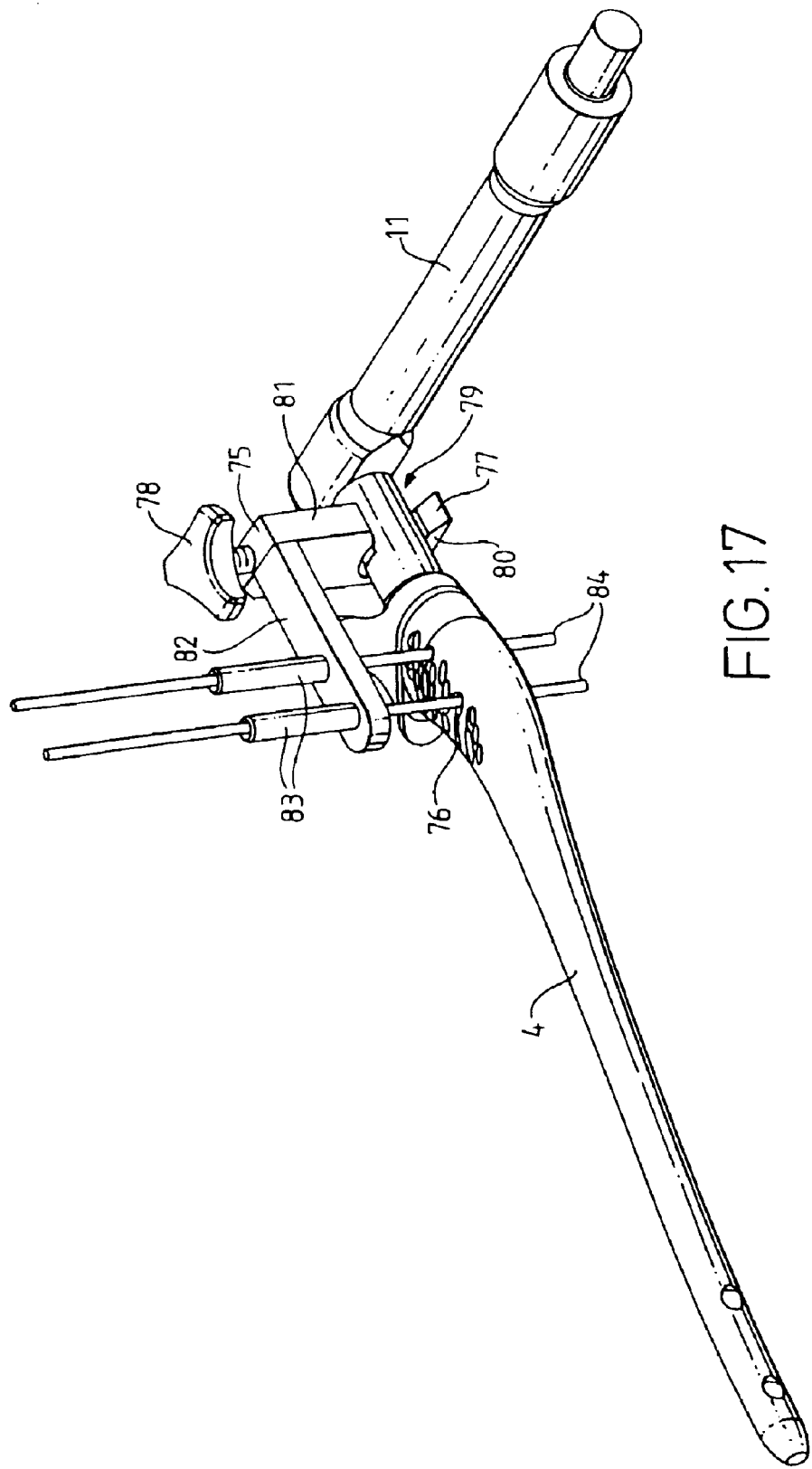
FIG. 17 is an isometric view showing a drill guide which can be clamped into position to enable holes to be made through the bone and soft tissue when it has been folded back into a position on the femur.

When the "window" is closed it is necessary to fold the soft tissue and bone which has previously been folded back to provide the window back into position and locate it around the installed prosthesis. FIG. 17 shows how a proximal drill guide 75 can be provided to guide drills through the folded back "flap" and to enable the drills to line up with pre-arranged holes 76 provided on the prosthesis 4. This device is in the form of an open jawed clamping block 77 which is provided with a tightening screw 78 which passes through a threaded bore (not shown) in the block to extend into the gap 79 provided between a lower clamping jaw 80 and an upper clamping jaw 81. The clamping block 77 carries an arm 82 which supports a pair of drill guides 83.

As will be seen from FIG. 17 the prosthesis is provided with a series of openings 76. With the prosthesis in support element 1 and held by second arm 11 the clamping block is placed in position and the drill guides are aligned by the use of guide rods or drills 84. With the drill guides now aligned with openings 76, the clamping screw 78 is tightened to lock the clamping block in position. The rods or drills 84 can now be removed, the "window" is closed and the drill guides employed to guide the drill or drills to make openings in the flap of bone and soft tissue 48. The openings can then be located by passing wire hoops through the openings and suitably locating them thus ensuring that the flap of material is held in place.

Figure 18:
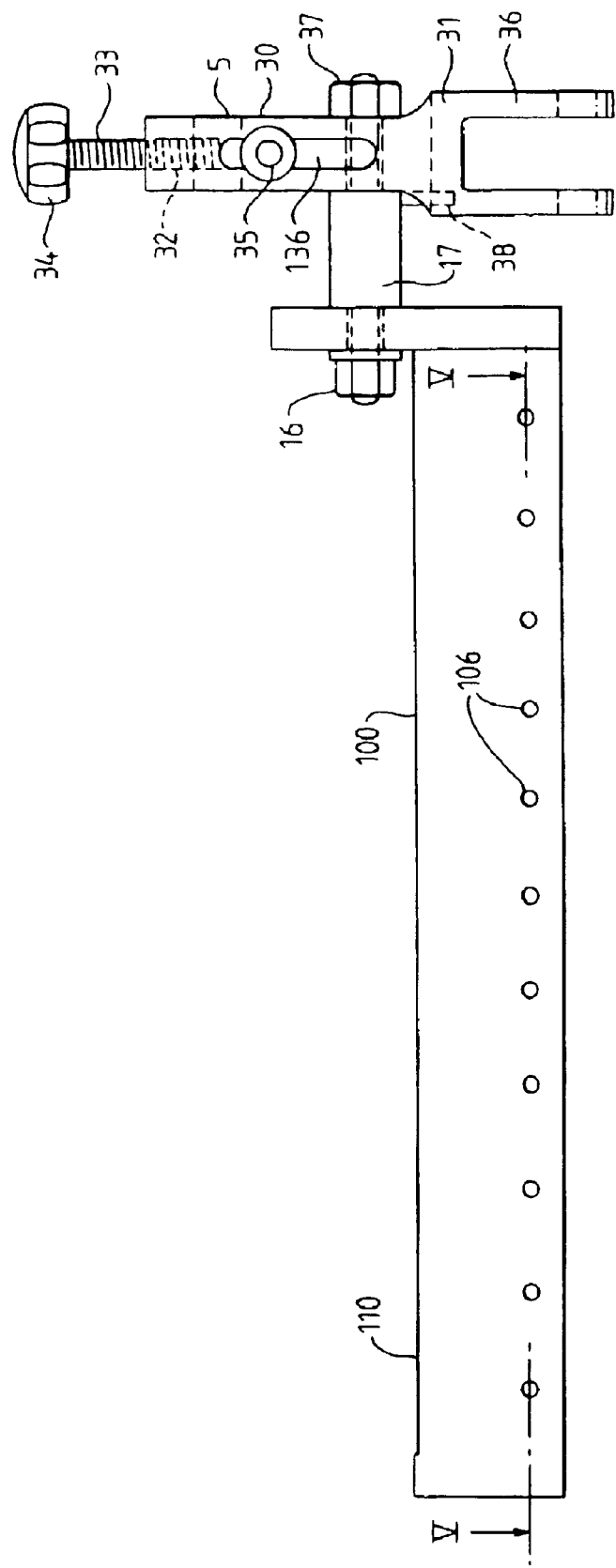
FIG. 18 is a front elevation of the clamp as shown in FIG. 10 attached to a drill guide element.
Figure 19:
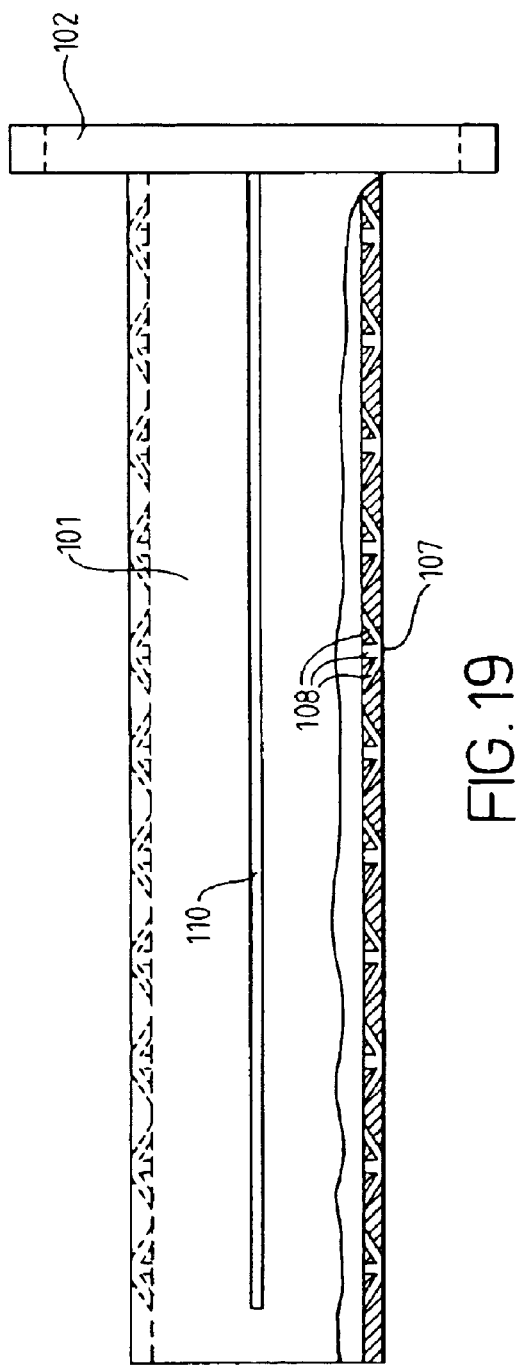
FIG. 19 is a plan view from above the drill guide element shown in FIG. 18 in part cross-section on the line V—V of FIG. 19.
Figure 20:
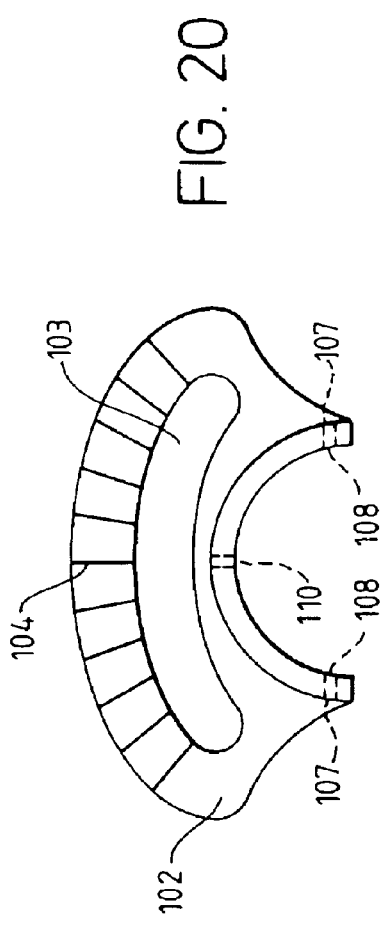
FIG. 20 is an end view of the drill guide element shown in FIG. 1.

FIGS. 18, 19 and 20 show apparatus for carrying out the first part of the transfemoral osteotomy surgery as shown in FIGS. 1 and 2 and utilizes the clamp device shown in FIGS. 9 and 10 for securing the support element to a resectioned femur. The apparatus includes a drill guide element 100 which is rigidly secured to the femur 6 by the open jawed clamp device which has a boss 17 located in a slot 40 in the body 30 and is held by nut 37 so that the position of the drill guide element 100 can be adjusted to alter the radial distance from the femur 6.

The drill guide element 100 comprises a semi-circular support 101 connected to a location bracket 102. This bracket 102 has a slot 103 through which the end of the boss 17 can extend, the bracket being held in position by the nut 16.

The surface of the bracket 102 is marked with graduations 104 to indicate the relative angular position between the two parts.

The drill guide element 100 includes a line of drill openings 106 along each side and which are adapted to guide a drill, the line of openings extending in a proximal/distal direction. Two parallel lines of drill openings are provided.

Adjacent drill openings 106 are angled in relation to each other as will be seen from FIG. 19 each of the entry points 107 on the outer side of the element serves three openings on the inner side of the element so that there are more entry points or openings on the inner side of the element than there are on the outer side. This enables a row of closely spaced openings to be drilled on each side.

A guide for guiding the instrument for exposing the femur along a proximal/distal line is also provided in the form of a guide slot 110 through which the surgeon can open soft tissue and subsequently saw the first longitudinally extending cut in the bone 6 after it has been previously transversely cut.

The apparatus is used for resectioning a femur when performing transfemoral osteotomy in the following manner. The surgeon first makes a transverse cut C to expose a proximal end of the femur which can be used as a reference point. This reference point end is exposed by the surgeon and the means for securing the drill guide element to the femur, that is the clamp, is placed in position by sliding the tines 36 around the bone ensuring that the guide disc 38 is close up against the severed end indicated by reference numeral 49. As mentioned above, the positioning is achieved with a rotative movement. Once in place the handle 34 is operated to close the clamp and maintain it in place. The drill guide element 100 is now placed and locked in position by nut 16. The element extends over the femur and the surgeon now opens the upper part of the femur by severing the soft tissue through the slot 101. This exposes the femur beneath it so that the surgeon can cut a proximal/laterally extending slot. The surgeon now drills a series of holes using the drill guide means through the soft tissue and into the bone. The row of holes in the bone provides a row of perforations which can be easily broken away to provide the side cuts M but leaving the two broken away parts of the bone still attached to the remainder by the soft tissue in the manner shown in FIG. 5.

The "window" now obtained can be used for the remainder of the operation and leaves the femur ready to receive the prosthesis.

Prior to opening the bone the drill guide element 100 will, of course, have been removed by releasing the nut 16 but the connector in the form of the clamp can be left in position. The same clamp is now used during the remainder of the operation to act as a connector for securing a support element provided with a drill guide to a prosthesis to be implanted and to a resectioned femur, and an adjuster for adjusting the angular position of the drill guide in relation to the resectioned femur about a proximal/distal axis as explained above.

The drill guide element can be used with the clamp in place on the targeting apparatus but if desired it can be removed and used separately with the drill guide element 100 as described above.

The targeting apparatus according to the invention provides a modular construction which includes a support element with a drill guide, a connector for securing it to a prosthesis, an alternative connector for securing it to the prosthesis, a clamp for securing it to the femur, a drill guide for drilling holes in the proximal end of the prosthesis and a drill guide for drilling a line of openings in the proximal-distal direction when preparing the "window" when performing transfemoral osteotomy surgery. The modular construction allows the various parts to be assembled together as required. Alternatively only some of the apparatus is required when performing endofemoral osteotomy surgery. When supplied as a complete kit the various parts can be assembled together as required at the time.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A targeting apparatus for use in implanting a prosthetic femoral component having through holes for receiving screws extending transverse to a longitudinal axis of the femur, comprising:
   a first arm extendable generally parallel to the longitudinal axis of the femur, said first arm having at least one drill guide thereon; and
   a second arm supported by said first arm, said second arm coupled to a proximal portion of said femoral component and shaped to extend around the greater trochanter and muscles of the hip joint.

2. The targeting apparatus as set forth in claim 1 wherein the drill guide is adjustable along the first arm.

3. The targeting apparatus as set forth in claim 1 further comprising a clamp support by said first arm for clamping on the femur.

4. The targeting apparatus as set forth in claim 3 wherein said clamp is supported on said first arm in a manner permitting adjustment along the longitudinal extend thereof.

5. The targeting apparatus as set forth in claim 4 wherein said clamp is slidably mounted on a longitudinal extending guide track formed on said first arm.

6. The targeting apparatus as set forth in claim 1 wherein said second arm is curved.

7. The targeting apparatus as set forth in claim 6 wherein said second arm is S-shaped.

8. The targeting apparatus as set forth in claim 1 wherein said second arm is capable of being coupled to a proximal end of the femur by a connector threadably engaging a threaded bore in a proximal end surface of the femoral component.

9. The targeting apparatus as set forth in claim 1 further comprising a means for adjusting an angular position of the drill guide in relation to the femur about a proximal-distal axis.

10. The targeting apparatus as set forth in claim 9 wherein the drill guide is located at a predetermined proximal-distal position from a means for coupling the second arm to a proximal end of the femoral component.

11. The targeting apparatus as set forth in claim 10 further comprising means for locating the drill guide in alternative proximal-distal positions on the first arm.

12. The targeting apparatus as set forth in claim 1 in which at least two drill guides are provided.

13. The targeting apparatus as forth in claim 1 wherein a drill guide has at least one line of drill openings each of which is adapted to guide a drill and means for rigidly securing the drill guide to a femur to be resectioned with the line of openings extending in a proximal-distal direction.

14. The targeting apparatus as set forth in claim 13 further comprising means for altering the angular position of the drill guide on the femur about a proximal-distal axis after it has been secured thereto.

15. The targeting apparatus as set forth in claim 13 wherein the drill guide includes two parallel lines of drill openings.

16. The targeting apparatus as set forth in claim 13 wherein adjacent drill openings are angled in relation to each other so that the openings are more closely spaced apart on an outer side of the drill guide than on an inner side adjacent the femur.

17. The targeting apparatus as set forth in claim 16 wherein each of the entry points of the openings on the outer side of the drill guide serves two or more openings so that there are more entry points for openings on the inner side of the drill guide than on the outer side.

18. The targeting apparatus as set forth in claim 13 wherein the drill guide also includes means for guiding means for exposing the femur along a proximal-distal line.

19. The targeting apparatus as set forth in claim 18 further including a guide means for guiding said means for exposing the femur.

20. The targeting apparatus as set forth in claim 19 wherein the guiding means is in the form of a guide slot.

21. The targeting apparatus as set forth in claim 13 wherein the drill guide element is removably connected to the securing means.

22. The targeting apparatus as set forth in claim 13 wherein the means for securing the drill guide to the femur is an adjustable open jawed clamp adapted to partially surround the femur with which it is to be used.

23. The targeting apparatus as set forth in claim 13 further comprising means for locating the securing means on a partially resectioned transverse end of the femur after a first transverse cut has been made.

* * * * *

UNITED STATES PATENT AND TRADEMARK OFFICE
CERTIFICATE OF CORRECTION

PATENT NO. : 6,783,535 B2
DATED : August 31, 2004
INVENTOR(S) : Nicolas Delogé et al.

It is certified that error appears in the above-identified patent and that said Letters Patent is hereby corrected as shown below:

Title page,
Item [57], ABSTRACT,
Line 7, "muscle" should read -- muscles --.

Column 7,
Line 25, "150" should read -- 15º --

Signed and Sealed this

First Day of February, 2005

JON W. DUDAS
*Director of the United States Patent and Trademark Office*